US006756795B2

(12) United States Patent
Hunt et al.

(10) Patent No.: US 6,756,795 B2
(45) Date of Patent: Jun. 29, 2004

(54) CARBON NANOBIMORPH ACTUATOR AND SENSOR

(75) Inventors: Brian D. Hunt, La Cresenta, CA (US); Flavio Noca, Altadena, CA (US); Michael E. Hoenk, Valencia, CA (US)

(73) Assignee: California Institute of Technology, Pasadena, CA (US)

( * ) Notice: Subject to any disclaimer, the term of this patent is extended or adjusted under 35 U.S.C. 154(b) by 240 days.

(21) Appl. No.: 10/052,302

(22) Filed: Jan. 18, 2002

(65) Prior Publication Data

US 2002/0180306 A1 Dec. 5, 2002

Related U.S. Application Data

(60) Provisional application No. 60/262,690, filed on Jan. 19, 2001.

(51) Int. Cl.[7] .......................... G01R 27/08; G21H 1/00
(52) U.S. Cl. .................. 324/701; 310/302; 290/1 R
(58) Field of Search ................... 810/300, 302, 810/311, 316.03, 339; 290/1 R; 324/419, 701; 216/52; 257/734, 79, 76, 24

(56) References Cited

U.S. PATENT DOCUMENTS

| 5,110,339 A | | 5/1992 | Ciriello et al. | |
| 5,837,115 A | | 11/1998 | Austin et al. | |
| 6,555,945 B1 | * | 4/2003 | Baughman et al. | 310/300 |

FOREIGN PATENT DOCUMENTS

| WO | WO 02/093738 A2 | 11/2002 |

OTHER PUBLICATIONS

Avrutsky, Ivan A. et al.; *Multiwavelength Diffraction and Apodization Using Binary Superimposed Gratings*; IEEE Photonics Technology Letters; vol. 10, No. 6, Jun. 1998; pp. 839–841.

Baughman, Ray H. et al.; *Carbon Nanotube Actuators*; Science; vol. 284; May 21, 1999; pp. 1340–1344.

Boul, P.J. et al.; *Reversible sidewall functionalization of buckytubes*; Chemical Physics Letters; vol. 310; Sep. 3, 1999; pp. 367–372.

Chen, Yan et al.; *Plasma–induced low–temperature growth of graphitic nanofibers on nickel substrates*; Journal of Crystal Growth; vol. 193; Jun. 5, 1998; pp. 342–346.

Choi, Young Chul et al.; *Growth of carbon nanotubes by microwave plasma–enhanced chemical vapor deposition at low temperature*; J. Vac. Sci. Technol., American Vacuum Society; vol. 18, No. 4; Jul./Aug. 2000; pp. 1864–1868.

(List continued on next page.)

Primary Examiner—N. Le
Assistant Examiner—Donald M. Lair
(74) Attorney, Agent, or Firm—Christie, Parker & Hale, LLP

(57) ABSTRACT

A nanomechanical actuator/oscillator device and system are provided. The nanomechanical actuator/oscillator device comprising nanobimorphs, such as nanotubes, designed such that inducing a difference in charge density between the tubes (e.g. by biasing one tube positive with respect to the other with sufficient tube-to-tube contact resistance) induces lateral movement in the end of the bimorph, forming a nanoscale resonator, as well as a force sensor when operated in an inverse mode. A method of producing a novel nanobimorph structure with integrated electrodes is also provided.

39 Claims, 6 Drawing Sheets

OTHER PUBLICATIONS

Chou, Hou–Pu et al.; *A microfabricated device for sizing and sorting DNA molecules*; Proc. Natl. Acad. Sci. USA, Applied Physical Sciences, Biophysics; vol. 96; Jan. 1999; pp. 11–13.

Dial, O. et al.; *Fabrication of high–density nanostructures by electron beam lithography*; J. Vac. Sci. Technol.; vol. 16, No. 6; Nov./Dec. 1998; pp. 3887–3890.

Drmanac, R. et al.; *Sequencing by Hybridization*; Adams M.D. et al. "Automated DNA sequencing and analysis" Academic Press; pp. 29–36 1994.

Duke, Thomas A. et al.; *Pulsed–field electrophoresis in microlithographic arrays*; Electrophoresis; vol. 17, 1996; pp. 1075–1079.

Duke, Thomas et al.; *Sequencing in nanofabricated arrays: A feasability study*; Electrophoresis; 1997; vol. 18, pp. 17–22.

Fan, Shoushan et al.; *Self–Oriented Regular Arrays of Carbon Nanotubes and Their Field Emission Properties*; Science; vol. 283; Jan. 22, 1999; pp. 512–514.

Hadd, Andrew G. et al.; *Sub–microliter DNA sequencing for capillary array electrophoresis*; Journal of Chromatography A; vol. 894; 2000; pp. 191–201.

Hafner, Jason H. et al; *Direct Growth of Single–Walled Carbon Nanotube Scanning Probe Microscopy Tips*; J. Am. Chem. Soc., The American Chemical Society; vol. 121; 1999; pp. 9750–9751.

Han, J. et al.; *Entropic Trapping and Escape of Long DNA Molecules at Submicron Size Constriction*; Physical Review Letters, The American Physical Society; vol. 83, No. 8; Aug. 23, 1999; pp. 1688–1691.

Han, Jie et al; *Observation and modeling of single–wall carbon nanotube bend junctions*; Physical Review B, The American Physical Society; vol. 57, No. 23; Jun. 15, 1998; pp. 983–989.

Han, Young–Soo et al.; *Synthesis of carbon nanotube bridges on patterned silicon wafers by selective lateral growth*; Journal of Applied Physics, American Institute of Physics; vol. 90, No. 11; Dec. 1, 2001; pp. 5731–5734.

Huang, Z.P. et al.; *Growth of highly oriented carbon nanotubes by plasma–enhanced hot filament chemical vapor deposition*; Applied Physics Letters, American Institute of Physics; vol. 73, No. 26; Dec. 28, 1998; pp. 3845–3847.

Hutt, Lester D. et al.; *Microfabricated Capillary Electrophoresis Amino Acid Chirality Analyzer for Extraterrestrial Exploration*; Analytical Chemistry; vol. 71, No. 18; Sep. 15, 1999; pp. 4000–4006.

Ilic, B. et al.; *Mechanical resonant immunospecific biological detector*; Applied Physics Letters, American Institute of Physics; vol. 77, No. 3; Jul. 17, 2000; pp. 450–452.

Ju, Jingyue et al.; *Energy transfer primers: A new fluorescence labeling paradigm for DNA sequencing and analysis*; Nature Medicine; vol. 2, No. 2; Feb. 1996; pp. 246–249.

Kelly, Ross T.; *Unidirectional rotary motion in a molecular system*; Nature; vol. 401; Sep. 9, 1999; pp. 150–152.

Kim, Philip et al.; *Nanotube Nanotweezers*; Science; vol. 286; Dec. 10, 1999; pp. 2148–2150.

Korgel, Brian A. et al.; *Self–Assembly of Silver Nanocrystals into Two–Dimensional Nanowire Arrays*; Advanced Materials; vol. 10, No. 9; 1998; pp. 661–665.

Koumura, Nagatoshi et al.; *Light–driven monodirectional molecular rotor*; Nature, vol. 401; Sep. 9, 1999; pp. 152–155.

Lee, Cheol Lin et al.; *Low–temperature growth of carbon nanotubes by thermal chemical vapor deposition using Pd, Cr, and Pt as co–catalyst*; Chemical Physics Letters; vol. 327; Sep. 15, 2000; pp. 277–283.

Li, Y.J. et al.; *Carbon nanotube films prepared by thermal chemical vapor deposition at low temperature for field emission applications*; Applied Physics Letters, American Institute of Physics; vol. 79, No. 11; Sep. 10, 2001; pp. 1670–1672.

Li, J. et al.; *Highly–ordered carbon nanotube arrays for electronics applications*; Applied Physics Letters, American Institute of Physics; vol. 75, No. 3; Jul. 19, 1999; pp. 367–369.

Liu, Q. et al.; *Detection of Virtually All Mutations–SSCP (DOVAM–S): A Rapid Method for Mutation Scanning with Virtually 100% Sensitity*; BioTechniques; vol. 26, No. 5; May 1999; pp. 932–942.

Masuda, Hideki et al.; *Highly ordered nanochannel–array architecture in anodic alumina*; Appl. Phys. Lett., American Institute of Physics; vol. 71, No. 19; Nov. 10, 1997; pp. 2770–2772.

Merkulov, V.I. et al.; *Patterned growth of individual and multiple vertically aligned carbon nanofibers*; Applied Physics Letters, American Institute of Physics; vol. 76, No. 24; Jun. 12, 2000, pp. 3555–3557.

Murakami, Hirohiko et al.; *Field emission from well–aligned, pattterned, carbon nanotube emitters*; Applied Physics Letters, American Institute of Physics; vol. 76, No. 13; Mar. 27, 2000; pp. 1776–1778.

Nakamura, S.; *InGaN–based violet laser diodes*; Semicond Sci. Technol.; vol. 14; 1999; pp. R27–R40.

Öttinger, Hans Christian; *A thermodynamically admissible reptation model for fast flows of entangled polymers*; The Society of Rheology, Inc.; J. Rheol; vol. 43, No. 6; Nov./Dec. 1999; pp. 1461–1493.

Poncharal, Philippe et al.; *Electrostatic Deflections and Electromechanical Resonance of Carbon Nanotubes*; Science; vol. 283; Mar. 5, 1999; pp. 1513–1516.

Ren, Z.F. et al.; *Growth of a single freestanding multiwall carbon nanotube on each nanonickel dot*; Applied Physics Letters, American Institute of Physics; vol. 75, No. 8; Aug. 23, 1999; pp. 1086–1088.

Reulet, B. et al.; *Acoustoelectric Effects in Carbon Nanotubes*; Physical Review Letters, The American Physical Society; vol. 58, No. 13, Sep. 25, 2000; pp. 2829–2832.

Roukes, M.L.; *Nanoelectromechanical Systems*; Technical Digest of the 2000 Solid–State Sensor and Actuator Workshop; pp. 1–10.

Routkevitch, Dmitri et al.; *Nonlithographic Nano–Wire Arrays; Fabrication, Physics, and Device Applications*; IEEE Transactions on Electron Devices; vol. 43, No. 10; Oct. 10, 1996; pp. 1646–1658.

Schmalzing, Dieter et al.; *Toward Real–World Sequencing by Microdevice Electrophoresis*; Genome Research; vol. 9; pp. 853–858 1999.

Soper, Steven A.; *Nanoliter–scale sample preparation methods directly coupled to polymethylmethacrylate–based microchips and gel–filled capillaries for the analysis of oligonucleotides*; Journal of Chromatography A; vol. 853; 1999; pp. 107–120.

Turner, S.W. et al.; *Monolithic nanofluid sieving structures for DNA manipulation*; J. Vac. Sci. Technol., American Vacuum Society; vol. 16, No. 6; Nov./Dec. 1998; pp. 3835–3840.

Van Der Gaag, B.P. et al; *Microfabrication below 10 nm*; Appl. Phys. Lett, American Institute of Physics; vol. 56, No. 5; Jan. 29, 1990; pp. 481–483.

Volkmuth, W.D. et al.; *DNA Electrodiffusion in a 2D Array of Posts*; Physical Review Letters, The American Physical Society; vol. 72, No. 13; Mar. 28, 1994; pp. 2117–2120.

Volkmuth, W.D. et al.; *DNA electrophoresis in microlithographic arrays*; Nature; vol. 358; Aug. 13, 1992; pp. 600–602.

Westermeier, Reiner; *Electrophoresis in Practice, A Guide to Method and Applications of DNA and Protein Separations, Chapter I—Electrophoresis*; Second Edition; VCH, A Wiley company; 1997; pp. 6–39.

Wildöer, Jeroen W.G. et al.; *Electronic structure of atomically resolved carbon nanotubes*; Nature; vol. 391; Jan. 1, 1998; pp. 59–62.

Xu, Yan; Capillary Electrophoresis; Analytical Chemistry, American Chemical Society; vol. 71, No. 12; Jun. 15, 1999; pp. 309R–313R.

Yoon, Dy et al.; *Comparison of chain conformations for ploystyrene and model molecules in the gas phase, solvents and melts from MD simulations*; Abstracts of Papers, Part 2: $215^{th}$ ACS National Meeting; American Chemical Society; Mar., 29–Apr. 2, 1998; 1 p.

Yu, Min–Feng et al.; *Tensile Loading of Ropes of Single Wall Carbon Nanotubes and their Mechanical Properties*; Physical Review Letters, The American Physical Society; vol. 84, No. 24; Jun. 12, 2000; pp. 5552–5555.

Zhang, Y. et al.; *Elastic Response of Carbon Nanotube Bundles to Visible Light*; Physical Review Letters, The American Physical Society; vol. 82, No. 17; Apr. 26, 1999; pp. 3472–3475.

Zhang, Yuegang et al.; *Electric–field–directed growth of aligned single–walled carbon nanotubes*; Applied Physics Letters, American Institute of Physics; vol. 79, No. 19; Nov. 5, 2001; pp. 3155–3157.

Zhang, Y et al.; *Formation of single–wall carbon nanotubes by laser ablation of fullerenes at low temperature*; Applied Physics Letters, American Institute of Physics; vol. 75, No. 20; Nov. 15, 1999; pp. 3087–3089.

* cited by examiner

Growth at 411 °C

Growth at 456 °C

Growth at 500 °C

Growth at 550 °C

CARBON NANOBIMORPH ACTUATOR AND SENSOR

CROSS-REFERENCE TO RELATED APPLICATION

This application is based on U.S. application No. 60/262,690, filed Jan. 19, 2001, the disclosure of which is incorporated by reference.

STATEMENT REGARDING FEDERALLY SPONSORED RESEARCH

The U.S. Government has certain rights in this invention pursuant to grant No. NAS 7-1407, awarded by the National Aeronautics and Space Administration, Office of Space Science.

FIELD OF THE INVENTION

The present invention is directed to a nanomechanical device, and more particularly to a nanomechanical device comprising self-assembled nanobimorphs for use as actuators, oscillators and sensors.

BACKGROUND OF THE INVENTION

This invention relates in general to nanomechanical devices comprising motion controllable self-assembled nanobimorphs, and in particular to self-assembled carbon nanobimorphs used as mechanical elements such as actuators and oscillators, or force detectors with single molecule sensitivity comprising a self-assembled carbon nanobimorph comprising at least two nanofeatures such as nanotubes arranged separately on a pair of electrodes for applying a potential across the bimorph for either measuring the characteristic motion of, or creating a characteristic motion in the nanobimorph.

Nanoscale structures are becoming increasingly important because they provide the basis for devices with dramatically reduced power and mass and enhanced capabilities. Practical nanotechnology-based applications will require nanoscale sensors and actuators for characterization and manipulation on the molecular scale. In addition, nanoscale elements that move will be essential for interfacing between the macro and nano-worlds: for fabrication of nanoscale structures, for characterization of those structures, and for coupling real-world inputs and outputs to molecular-scale electronics.

Nanoscale mechanical structures would also enable the fabrication of high-quality-factor (Q) mechanical resonators with high mechanical responsivity. Such devices can form very low-loss, low-phase-noise oscillators for filters, local oscillators, and other signal processing applications. High-Q resonators are critical components in communications and radar systems, as well as in MEMS-based sensors such as a micro-gyroscope. The combination of high-Q with small force constants enabled by nanoscale resonators would also produce oscillators with exceptional force sensitivity. This sensitivity is important for a variety of force-detection-based sensors and may ultimately allow single molecule spectroscopy by NMR and optical techniques.

Nanoscale actuators and oscillators are also key components of mechanical signal processing systems. For example, actuators can be used to produce switches and mechanical transistors, while oscillator arrays containing elements with controllably varying resonant frequencies form the basis for high-speed Fourier analysis, similar to the frequency-dependent signal processing done in biological hearing systems. Mechanical signal processing is of great interest because small-scale, high-Q mechanical elements may theoretically enable processing at GHz rates with orders-of-magnitude lower power dissipation than conventional CMOS processors.

The emerging carbon nanotube technology offers exciting possibilities for producing useful nanoscale actuators and mechanical oscillators. Probing and manipulating on the molecular scale will require tools of a similar size. Carbon nanotubes provide a unique bridge between the macroscopic and nano-worlds because they have nanometer cross-sectional dimensions combined with tube lengths that can reach fractions of a millimeter. Nanotubes are well suited for use as robust, high-Q oscillators, because they possess near perfect molecular bonding coupled with extremely high tensile strength, and they exhibit elastic deformation even at high bending angles.

Despite the potential for these nanomechanical devices, the practical application of nanotube-based actuators and oscillators has been limited by the development of growth and processing methods for control of nanotube placement and orientation. These techniques are critical for a wide variety of other nanotube applications including nanotube electronic systems.

One novel approach to making nanometer-scale structures utilizes self-assembly of atoms and molecules to build up functional structures. In self-assembled processing, atom positions are determined by fundamental physical constraints such as bond lengths and angles, as well as atom-to-atom interactions with other atoms in the vicinity of the site being occupied. Essentially, self-assembly uses the principles of synthetic chemistry and biology to Agrow@ complex structures from a set of basic feedstocks. Utilizing such techniques molecular motors have been synthetically produced containing fewer than 80 atoms. Chemical vapor deposition (CVD) appears to be the most suitable method for nanotube production for sensor and electronic applications. CVD uses a carbon-containing gas such as methane, which is decomposed at a hot substrate surface (typically 600–900 C) coated with a thin catalyst film such as Ni or Co. However, most studies to date have produced disordered nanotube films.

A notable exception is the work of Prof. Xu who has developed a new technique for producing geometrically regular nanotube arrays with excellent uniformity in nanopore templates. Xu et al. *Appl. Phys. Lett.*, 75, 367 (1999), incorporated herein by reference. Post-patterning of these ordered arrays could be used to selectively remove tubes in certain areas or produce regions with different length tubes. A variety of other studies have shown that dense, but locally disordered arrays of normally-oriented nanotubes can be selectively grown on pre-patterned catalyst layers. However, none of the current techniques have been able to grow vertical individual nanotubes or small groups of nanotubes with integrated electrodes, as would be necessary to form nanotube oscillators or actuators.

In addition, there has been little progress in the control of nanotube orientation in the plane parallel to the substrate surface. Many of the basic electrical measurements of nanotubes have been done using electrodes placed on randomly scattered tubes after growth, or by physically manipulating tubes into place with an atomic force microscope (AFM). Dai and co-workers have been able to demonstrate random in-plane growth between closely spaced catalyst pads, including growth over trenches, as well as a related technique to produce nanotubes suspended between Si posts.

Dai. Et al., *Science*, 283, 512 (1999), incorporated herein by reference. In these cases individual nanotubes sometimes contact adjacent electrodes by chance, and excess tubes can be removed with an AFM tip. This type of procedure can be effective for simple electrical measurements, but considerable improvements will be required for production of more complex nanotube circuits. Smalley's group has demonstrated a wet chemistry-based method of control over nanotube placement using solution deposition on chemically functionalized substrates, although questions remain about nanotube length control and contact resistance. Smalley et al., *Nature*, 391, 59 (1998), incorporated herein by reference. However, none of the current techniques have been able to grow vertical individual nanotubes or small groups of nanotubes with integrated electrodes, as would be necessary to form nanotube oscillators or actuators.

In addition to the problems associated with controlled growth and orientation of nanotubes, nanotube actuators and oscillators also require a transduction mechanism to convert input signals to physical motion and to provide corresponding output signals.

One possible mechanism is suggested by a recent demonstration that nanotube mats can serve as very high efficiency electromechanical actuators in an electrolyte solution, with the possibility of even better results for well-ordered single wall tubes. Baughman et al., *Science*, 284 1340 (1999), incorporated herein by reference. Other potential actuation mechanisms to be investigated include light-induced nanotube motion, which has been observed, and magnetomotive actuation. However, these techniques have only been demonstrated for large disordered arrays of nanotubes, no technique has been developed for the controlled motion of individual nanotube bimorphs.

Accordingly, a need exists to develop nanoscale mechanical devices, such as, actuators and oscillators to enable applications ranging from molecular-scale characterization and manipulation, to ultra-low-loss mechanical filters and local oscillators for communications and radar, to rad-hard low-power mechanical signal processors.

SUMMARY OF THE INVENTION

The present invention is directed to a nanomechanical device and system utilizing nanobimorphs comprising at least two adjacent nanofeatures, such as nanotubes, in a touching relation at one end, and means for inducing a difference in charge density between the tubes (e.g. by biasing one tube positive with respect to the other with sufficient tube-to-tube contact resistance) such that lateral movement is induced in the end of the bimorph, forming a nanoscale actuator, as well as a force sensor when operated in an inverse mode. The invention is also directed to growth techniques capable of producing a novel nanotube bimorph structure with integrated electrodes.

In one embodiment this invention utilizes a nanobimorph with an integrated electrode substrate that functions as an oscillator or actuator. This invention is also directed to a device which utilizes a nanobimorph with an integrated electrode substrate that functions as a molecular sensor. This invention is also directed to novel systems and methods for utilizing devices comprising at least one nanobimorph with an integrated electrode substrate.

In another embodiment, the invention is directed to a nanobimorph actuator comprising a nanobimorph with an integrated electrode substrate. The nanoscale actuators of the present invention are designed to provide the capability of controllable motion on near-atomic scales. In such an embodiment, the transduction mechanism is symmetric—length changes in the nanotubes will induce charge transfer and hence voltages, providing a readout mechanism for the actuators.

In another alternative embodiment, the induced voltage is produced by optical irradiation.

In still another embodiment, the invention is directed to nanobimorph oscillators or resonators. The nanobimorph oscillators may be utilized as high-Q mechanical resonators for filters, signal processing, and sensors. In such an embodiment, excitation and readout of a nanobimorph oscillator may be made using the actuation methods previously discussed in the nanobimorph actuator section: piezoelectric, light, or electrostatic.

In yet another embodiment, the invention is directed to mechanical signal processing systems utilizing the nanobimorph actuators and oscillators of the current invention. For example, in one embodiment, actuators can be used to produce switches and mechanical transistors, while in another embodiment oscillator arrays containing elements with controllably varying resonant frequencies form the basis for high-speed Fourier signal processing.

In still yet another embodiment the nanotubes comprising the nanobimorph self-assemble into the nanobimorph having a specified diameter and height suitable for use in the devices of the current invention.

In still yet another embodiment, the substrate is made of a semiconductor such as, for example, oxidized silicon or aluminum oxide, coated with a metal catalyst film such as, for example, Ni or Co. In this embodiment, the silicon can be further doped to adjust the electronic properties of the substrate surface.

In still yet another embodiment, the nanotubes comprising the nanobimorph are self-assembled from an inert material such as, for example, carbon utilizing a carbon feedstock gas such as, for example, ethylene.

In still yet another embodiment, the invention is directed to a system for the detection of substances comprising multiple detectors as described above, such that parallel processing of molecules can be carried out.

In still yet another embodiment, the invention is directed to growth and processing techniques to control nanobimorph location and orientation; and methods for positioning nanotubes during growth, including nanoscale patterning of catalyst dots to seed the growth of vertical nanotubes on integrated electrodes.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention is directed to a device and system utilizing nanobimorphs comprising at least two nanofeatures, such as nanotubes, and means for inducing a difference in charge density between tubes (e.g. by biasing one tube positive with respect to the other with sufficient tube-to-tube contact resistance) such that lateral movement is induced in the end of the bimorph, forming a nanoscale actuator/oscillator, as well as a force sensor when operated in an inverse mode. These devices will be collectively referred to as nanomechanical devices herein.

Figure 1:
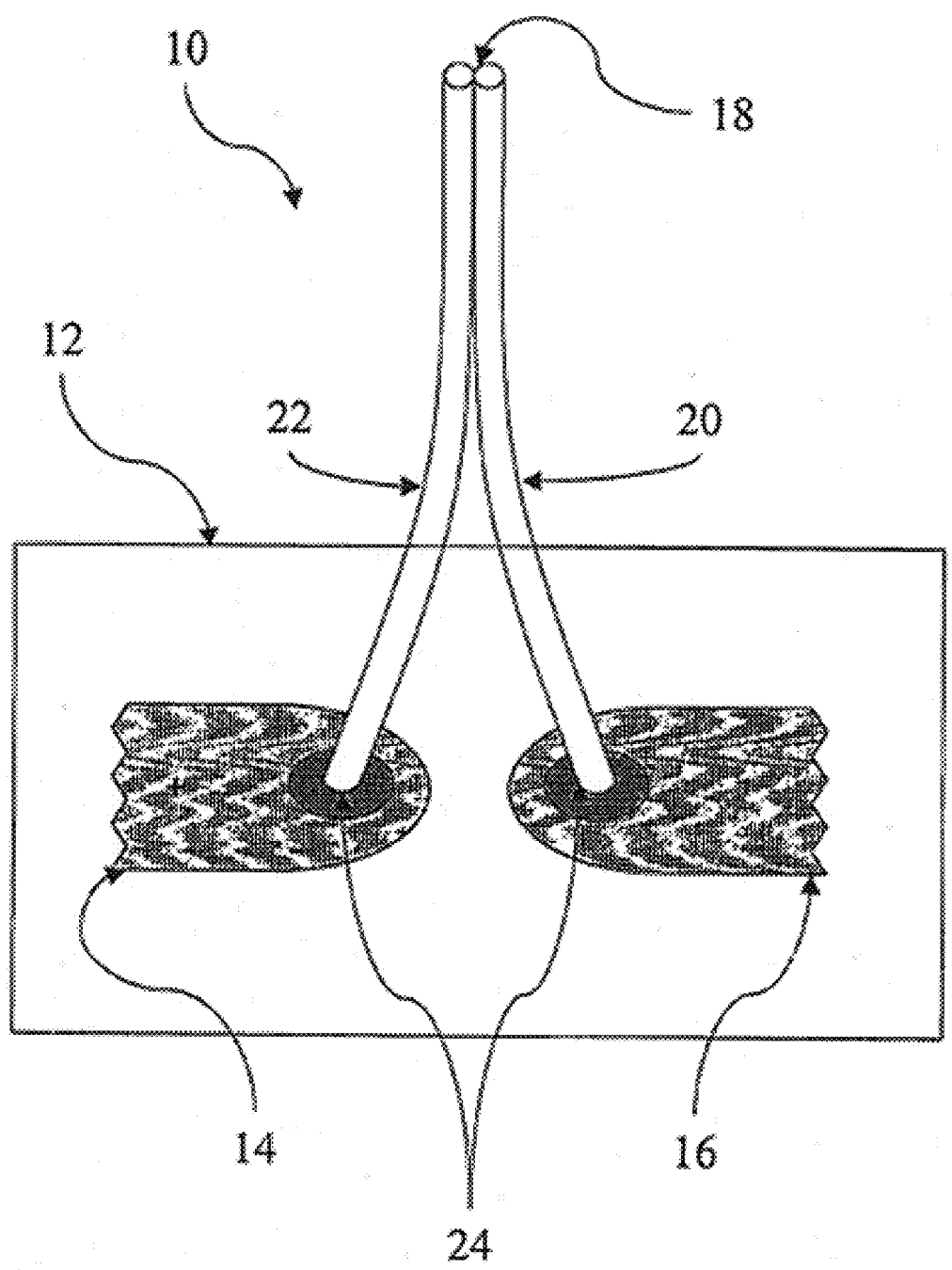
FIG. 1 is a schematic view of an embodiment of a nanobimorph according to the invention.

As shown in FIG. 1, the nanomechanical device 10 according to the invention generally comprises a substrate 12, having first 14 and second 16 electrodes, and nanobimorph 18, comprising first 20 and second 22 self-assembled nanotubes arranged on nucleation points 24 on the first 14 and second 16 electrodes of the substrate 12 such that the nanotubes are spaced apart from each other at an end proximal to the substrate and attractively attached at an end distal from the substrate.

Figure 2:
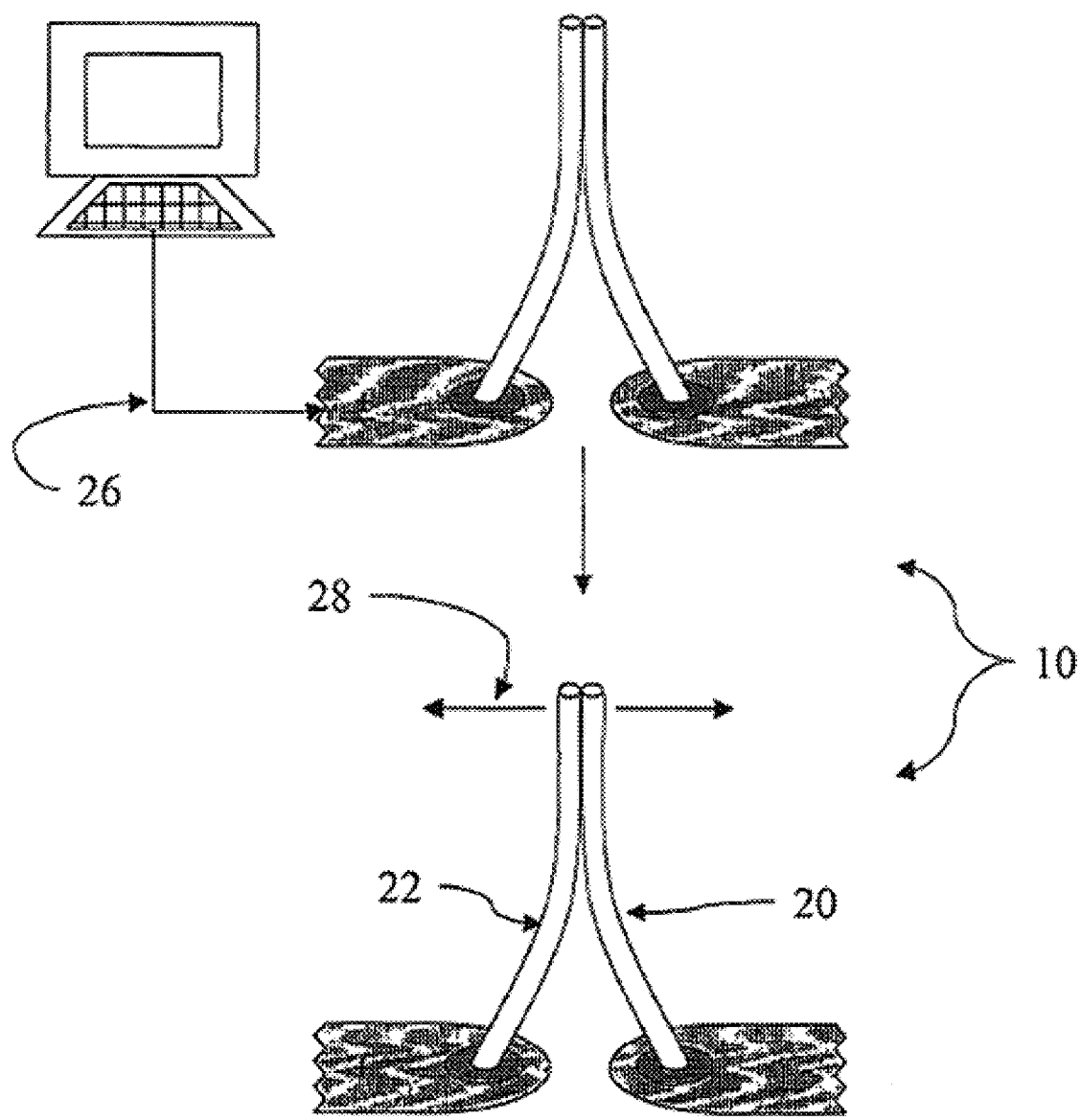
FIG. 2 is a schematic view of an embodiment of a nanobimorph in operation as an actuator or oscillator according to the invention.
Figure 3:
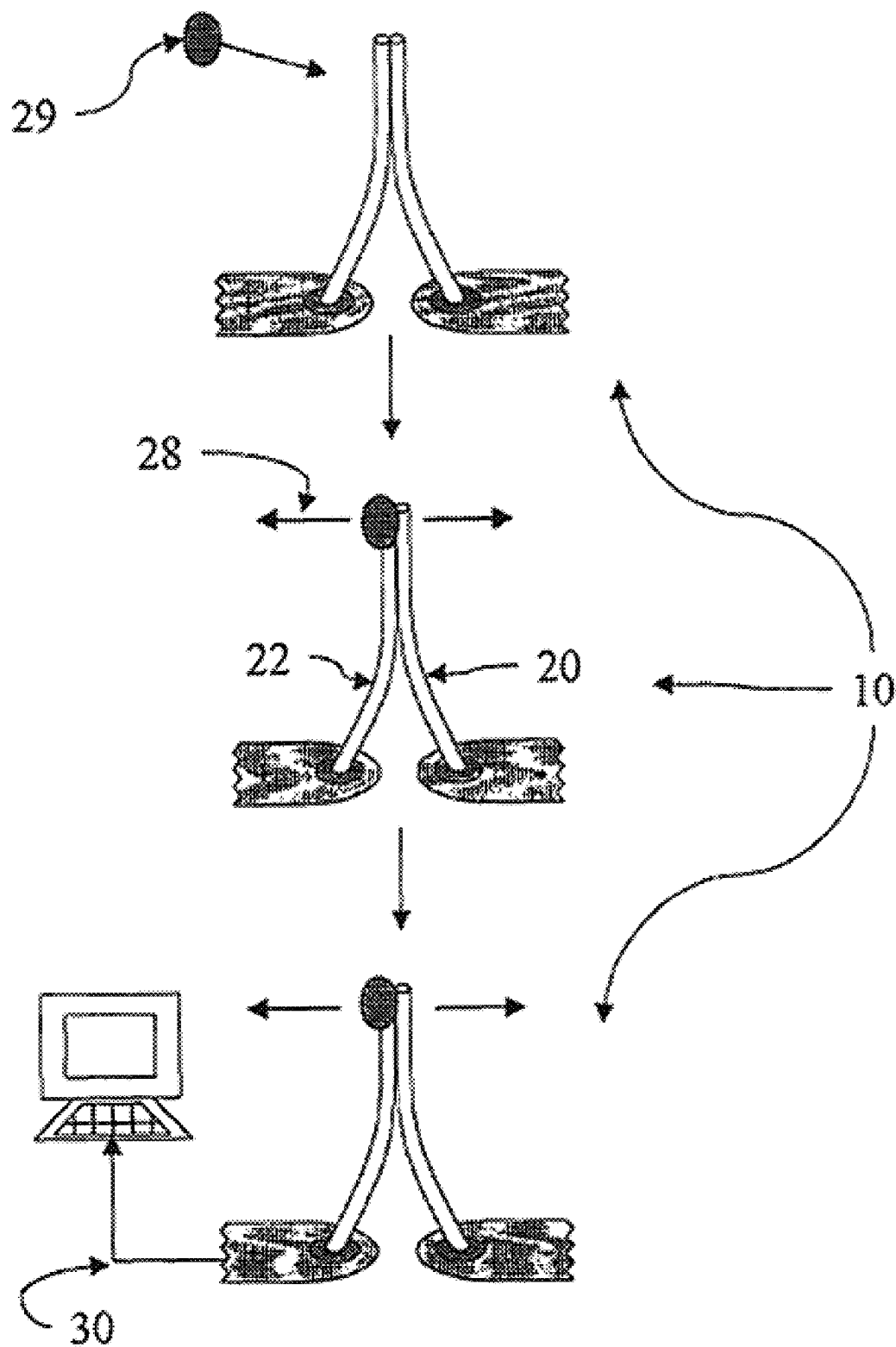
FIG. 3 is a schematic view of an embodiment of a nanobimorph in operation as a sensor according to the invention.

The nanomechanical device shown schematically in FIG. 1 has two basic modes of operation: an actuator/oscillator mode, shown in FIG. 2 and a sensor mode shown in FIG. 3. As shown in FIG. 2, in the actuator mode, the nanobimorph 10 acts as a transducer, converting an input signal 26 into a mechanical action 28. In this embodiment, a voltage is applied between the nanotubes with sufficient tube-to-tube contact resistance to create a charge difference and thereby produce a deflection of the bimorph structure, corresponding to an expansion for the negatively-biased tubes 20 and a contraction for the positively-biased tubes 22. As shown in FIG. 3, when the nanobimorph 10 is operated in the inverse mode, subtle changes in the position of the nanotubes, i.e., a deflection 28 cause by an impinging molecule 29 will induce a voltage across the two nanotubes producing an output signal 30 which can be measured by an external monitoring device 32 in signal communication with the electrodes 14 and 16 of the bimorph 10. In addition, the nanobimorph can act as a molecular detector when operating as an oscillator by measuring shifts in the mechanical resonance frequency induced by attached molecules. Such a detector can be made to be chemically specific by functionalizing the nanotubes to attach to specific molecules.

The charge induced motion and motion induced charge discussed above have previously been observed in random arrays of carbon bimorph mats and in graphite sheets, see, e.g., R. Baughman, cited above, incorporated herein by reference. Although not to be bound by theory, it is believed that the nanotube length change is caused by "quantum chemical effects", that is, changes in orbital occupation and band structure result in changes in the C—C bond distances and thus the length of the nanotube. It should also be noted that the charge-induced transduction mechanism is symmetric, i.e., length changes in the nanotubes will induce charge transfers and hence voltages, providing a readout mechanism and/or positional sensor for both actuators and oscillators. Although the Baughman experiments were done in electrolytic solutions, it should be understood that no electrolytic solution is required so long as direct electrical contact is made with each nanotube. Alternatively, although the charge-induced actuation mechanisms shown in FIGS. 1 to 3 are only depicted in non-liquid environments, which are useful for high-Q oscillator applications, it should be understood that the nanotube electromechanical transduction effect can be compatible with operation in liquids, such as for use in biological actuators.

Any nanofeature suitable for use as an actuator/oscillator bimorph may be utilized in the current invention. In a preferred embodiment, as shown in FIGS. 1 to 3 and discussed above, a carbon nanotube bimorph is utilized. Carbon nanotubes possess a combination of properties that make them well suited for use as nano-actuators. For example, nanotubes combine a nanometer scale diameter with a large aspect ratio, good electrical conductivity, and elastic bending. Single-wall nanotubes also have a Young's modulus of approximately 1 TPa, which corresponds to strength/weight ratio approaching 200 times that of steel. The combination of this high Young's modulus and the ability to withstand large strains (~5%) suggests that SWNTs should also have very high breaking strengths. These properties indicate that nanotubes can interact at the nanoscale level, but are also long enough and strong enough to couple efficiently to the macro-world. In addition, the observed electromechanical response of these initial nanotube actuators is quite large. For example, it has been observed that nanotube sheets exhibit significantly larger stresses than human muscle and higher strains than the best ferroelectric materials. In fact, carbon nanotubes have a volumetric work capacity that is more than 29 times higher than any other known material.

Even though such electrode or direct control deflection could be utilized for low-frequency motion, higher frequency electrostatic drive for nanoscale structures may be limited by parasitic capacitances. However, it is well known that C nanotubes show a direct coupling between optical irradiation and their mechanical properties. Accordingly, in an alternative embodiment an optical based actuation technique could is utilized for coherent stimulation of nanotube arrays for mechanical signal processing applications.

Although the above discussion has been directed to the actual nanotube bimorph actuator according to the present invention, it should be understood that the invention is also directed to suitable nanomechanical devices comprising the nanobimorph actuators shown schematically in the above figures. For example, nanoscale actuators provide the capability of controllable motion on near-atomic scales, and as such, these devices provide the basis for characterization, manipulation, and fabrication at sizes less than 100 nm. Some exemplary applications include: characterization of individual molecules by chemical AFM with functionalized nanotube probes, and even actual assembly of custom molecules and nanoscale structures. In short, the nanobimorph actuators according to the present invention provide small-scale elements that move in response to an input signal which in turn provide the means for interfacing the macroscopic and molecular worlds.

In other embodiments, nano-actuators of the current invention could be utilized as macro-inputs to control and measure nanoscale structures, and could serve as I/O couplers to molecular computers. For example, one implementation of a Quantum Cellular Automata (QCA) computer relies on the bistable positioning of electron pairs. In such an embodiment, the position state of a local pair could be switched or read out by mechanical flipping of a molecular dipole by a nano-actuator. In another alternative embodiment, nanometer-scale actuators could be utilized to provide the means for motion of cell-sized robots. Finally, in another alternative embodiment, nano-actuators could be used to fabricate components for low-power mechanical signal processing, such as nano-relay switches and mechanical transistors.

Although the above discussion has focussed on nano-actuator embodiments of the invention, the mechanical resonators can also be utilized as high quality oscillators. The natural rigidity and structural perfection of the nanotubes, discussed above, indicates that the nanobimorph system according to the present invention should function as a high-Q mechanical resonator for many devices, such as, for example, filters, signal processors, and sensors. Since nanotubes naturally occur with nanoscale diameters, they are well suited for fabrication of oscillators with large aspect ratios and associated high responsivity. The lowest order resonant frequency for a nanotube cantilever is given by:

$$v_j = \frac{(1.875)^2}{8\pi} \frac{1}{L^2} \sqrt{D^2 + D_i^2} \sqrt{\frac{E_b}{\rho}} \quad (1)$$

where L is the length, D and $D_i$ are the outer and inner diameters, $E_b$ is the elastic modulus, and is the density (1.33 g/cm$^3$). For a cantilever with D=10 nm, $D_i$=8 nm, and 100 nm in length, this formula predicts a resonant frequency of approximately 4 GHz. This frequency would more than double for a nanotube oscillator fixed on both ends. Note that since nanotube lengths can be varied over the range of approximately 10 nm to 100 μm, we should be able to control resonant frequencies over 8 orders of magnitude.

Such nano-structures also exhibit extremely high quality factors, for example, Q values of mechanical oscillators range from $10^3$ to $10^9$, with values of $10^3$ to $10^5$ for nanoscale structures in vacuum. These Qs are much larger than typical quality factors for electronic resonant circuits, accordingly, mechanical resonators such as quartz crystal oscillators are used in communications systems. Because Q varies as 1/D, where D is the internal dissipation, high Q values correspond to low-loss system components. High quality factors also translate to exceptional oscillator stability and low phase noise. Such low-phase-noise local oscillators (LO) are critically important for narrow-bandwidth communications and sensitive doppler radars. For example, the LO phase noise sets the minimum detectable velocity for Doppler radar. In another embodiment, such high-Q oscillators could also be utilized as narrow-band, low-loss filters, and improve the stability and sensitivity of MEMS-based sensors such as a micro-gyroscope.

Moreover, by moving to nanoscale mechanical structures, it is possible to combine high Qs with high frequency operation and small force constants (high responsivity). Calculations indicate that Si mechanical oscillators with realistically achievable dimensions (0.1×0.01×0.01) have resonant frequencies of a few GHz. High resonant frequencies are important for producing mechanical signal processing components compatible with today's characteristic circuit clock rates. Resonators with nanoscale dimensions can achieve GHz resonant frequencies in structures with reasonably large aspect ratios, which translates directly to small force constants. The combination of high-Q with small force constants enabled by nanoscale resonators results in oscillators with exceptional force sensitivity. Accordingly, in one embodiment the nano-resonator may be utilized in the inverse mode for a variety of force-detection-based sensors and if properly functionalized allows for the possibility of single molecule spectroscopy by NMR and optical techniques.

Although optical read-out techniques are discussed above, excitation and readout of a nanobimorph oscillator could be done using the actuation methods previously discussed in relation to the nanobimorph actuator embodiment: charge-induced transduction, light, or electrostatic. In addition, for a nanobimorph oscillator attached to electrodes at both ends, it is possible to use a "magnetomotive" technique, in which the Lorenz-force interaction between an alternating current flowing in the oscillator beam and a magnetic field applied normal to the beam generates a force perpendicular to the beam and applied field. The transverse motion of the beam in turn produces an induced voltage along the length of the beam, which can be detected by a network analyzer.

The signal monitor system for any of the above detection schemes can comprise any suitable circuit or device capable of measuring the signal change from the detector and transmitting that information to the user, such as, for example, a printed circuit board having a pre-amplifier, an AD converter and driver circuit, and a programmable chip for instrumentation specific software; or a multichip module comprising those elements.

In another embodiment, the nanoscale actuators and oscillators discussed above may also be utilized in mechanical signal processing systems. Mechanical signal processing is of great interest because small-scale, high-Q mechanical elements theoretically enable processing at GHz rates with up to six orders of magnitude lower power dissipation than conventional CMOS processors of comparable complexity. In addition, such devices would be radiation tolerant, an important property for space-based applications. For example, in one embodiment, a nanobimorph actuator according to the invention can be used to produce switches and mechanical transistors. In another embodiment, a nanobimorph oscillator array according to the invention containing elements with controllably varying resonant frequencies could be utilized for high-speed Fourier signal processing, mimicking the mechanical processing that occurs in mammalian ears.

Returning to the structure of the underlying nanobimorph system 10, shown in FIGS. 1 to 3, it should be understood that the substrate 12 can be made of any material which can withstand the temperatures required for growth of the nanotubes 20 and 22 and which can be modified to provide suitable ordered pairs of nucleation points 24 for growing the nanotubes 20 and 22 of the nanomechanical device 10, such as, for example, metallized Si oxide wafers, anodized alumina, glass, or even polymeric plastics. In turn, any suitable electrode and catalyzing metal can be used for the electrodes 14 and 16 and to activate the nucleation points 24 on the surface of the substrate 12, such as, for example, nickel or cobalt. Alternatively, the catalyzing metal could be an alloy of two or more metals such as a Co/Ni or Ti/Ni alloys. The metal catalysts could also be produced by pyrolysis of inorganic or organic metal-containing compounds, such as, for example, Ferric Nitrate or Cobalt Chloride. Accordingly, in the limit of sub-50 nm catalyst dots 24, it is possible to nucleate growth of a single nanotube 20 or 22 at each catalyst location. Integrated electrodes 14 and 16 can be produced by combining the catalyst dots with non-catalytic electrodes. This ability to precisely locate individual nanotubes and make electrical contact to each tube provides the basis for fabrication of vertically aligned bimorph and oscillator structures. Such a method may utilize an electron-beam lithography system.

Figure 4A:
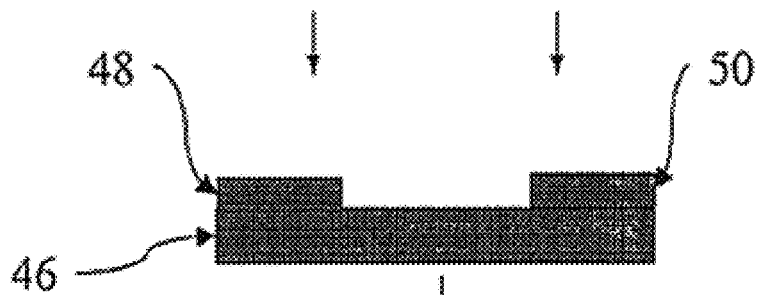
FIG. 4a is a schematic view of an embodiment of a process for forming a nanobimorph according to the invention.
Figure 4B:
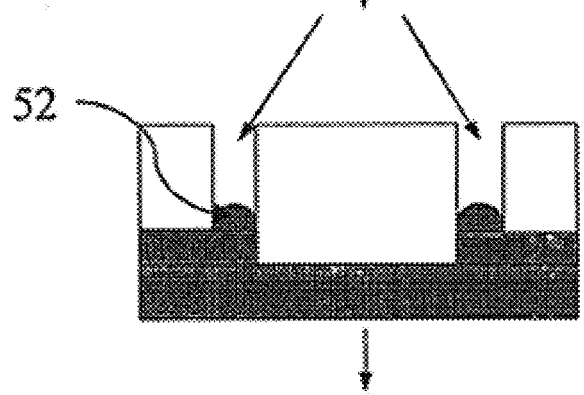
FIG. 4b is a schematic view of an embodiment of a process for forming a nanobimorph according to the invention.
Figure 4C:
FIG. 4c is a schematic view of an embodiment of a process for forming a nanobimorph according to the invention.
Figure 4D:
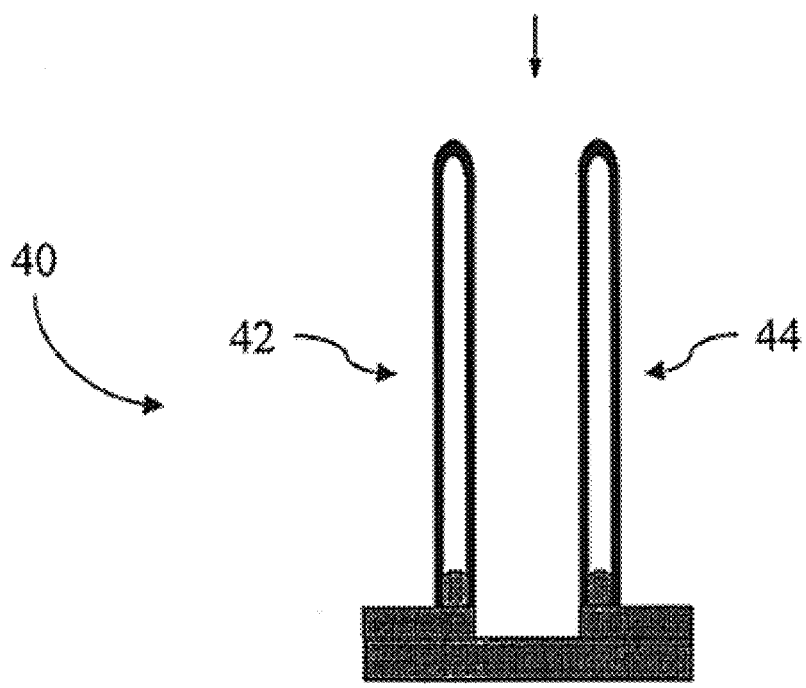
FIG. 4d is a schematic view of an embodiment of a process for forming a nanobimorph according to the invention.

One possible process for forming the nanomechanical device 40 of the present invention comprising nanotube bimorphs 42 and 44 utilizing a chemical vapor deposition (CVD) technique is shown schematically in FIGS. 4a to 4d. In a first step, as shown in FIG. 4a, a substrate 46, such as, for example, silicon is coated with a high purity metal film, such as, for example, Ti. The metal is then patterned in a multistep process to produce electrodes 48 and 50 in ordered pairs on the substrate 46. Next, a small amount of catalytic material 52, such as, for example, Co or Ni is deposited by electrochemical means or by physical vapor deposition on electron-beam defined catalyst patterns on the electrodes to serve as a catalyst for carbon nanotube 42 and 44 growth, as shown in FIG. 4b. As shown in FIG. 4c, the electrodes and catalyst are partially exposed by dissolving away the electron beam resist in an appropriate solvent such as acetone. Finally, as shown in FIG. 4d, the nanotubes 42 and 44 are self-assembled by pyrolysis of a suitable feedstock, such as, for example, ethylene gas diluted in nitrogen and/or ammonia and/or hydrogen at about 650 C. The electrodes 48 and 50 and the catalyzed dots 52 serve as a template such that the nanotubes 42 and 44 self-assemble in a bimorph pair corresponding to the dots 52 in the anodized metal substrate 46. After the adjacent nanotubes 42 and 44 have grown sufficiently to allow interaction, the van der Waals attraction between the adjacent tubes is sufficient to ensure that the tubes will become attached along their sidewalls at their distal ends, as shown in FIGS. 1 to 3.

A potential embodiment of the invention includes a modification of the nanotube growth process to increase the contact resistance between the two tubes in the bimorph by including an additional gas or gases such as fluorine, for example. Post growth treatments using appropriate gases or liquids can also serve the same purpose.

Although one method for the self-assembly of carbon nanotubes is described above, it should be understood that in order to incorporate the carbon nanotube bimorph actuators and oscillators on CMOS electronics it is necessary to provide carbon nanotube growth at temperatures compatible with processed CMOS circuits, i.e., below about 500° C. Although any suitable method of low temperature growth may be utilized, some exemplary methods include: 1) Murikami et al. (*Appl. Phys. Lett.* 76(13), 1776 (2000)) method for growing aligned carbon nanotube arrays for field emission at <600° C. using bias-enhanced microwave plasma CVD on patterned, nickel-based catalyst at 1–3 Torr; 2) Li et al. (*Appl. Phys. Lett.*, 79(11), 1670 (2001)) method of unaligned nanotube growth on glass at 570° C. using CVD at 100 Torr; 3) low temperature processes for growing carbon nanotubes on silicon (Choi et al., *J. Vac. Sci. Technol. A*, 18(4), 1864 (2000)): using 70 nm nickel films as a catalyst deposited on silicon substrates coated with TiN as an adhesion enhancement layer) and silicon dioxide (Lee et al., *Chem. Phys. Lett.* 327, 277 (2000)) between 500–550° C.; 4) Zhang and Iijima (*Appl. Phys. Lett.*, 75(20), 3087 (1999)) method for growing single-walled carbon nanotubes at 400 C using laser ablation technique with powdered catalyst containing Ni—Co; and 5) Chen et al. (*J. Cryst. Growth*, 193, 342 (1998)) method of growing graphitic nanofibers on nickel substrates at 350–400° C. All of which are incorporated herein by reference.

Figure 5:
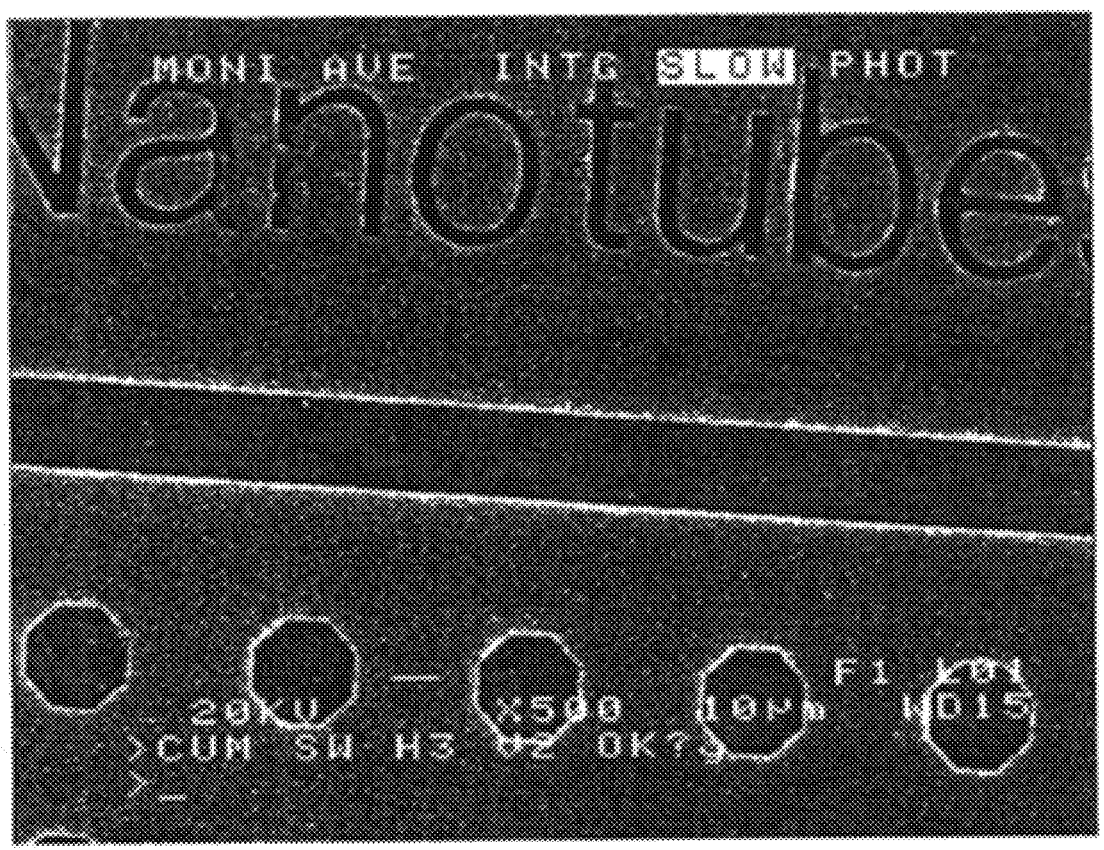
FIG. 5 is an SEM image of an embodiment of spatially ordered nanotube growth according to the invention.
Figure 6A:
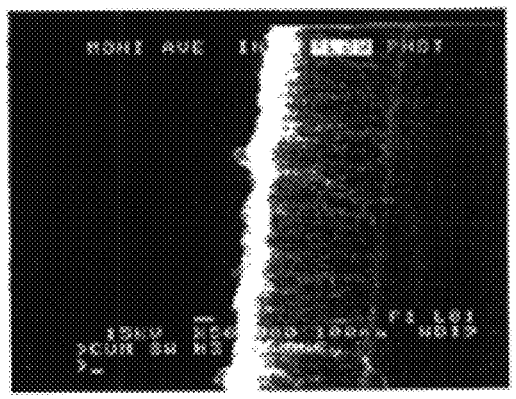
FIG. 6a is an SEM image of an embodiment of nanotubes grown at a temperature of 411° C. according to the invention.
Figure 6B:
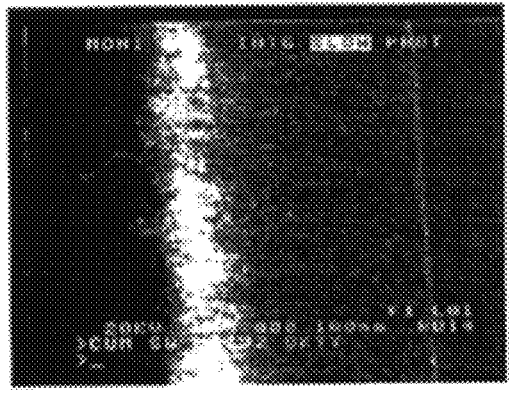
FIG. 6b is an SEM image of an embodiment of nanotubes grown at a temperature of 456° C. according to the invention.
Figure 6C:
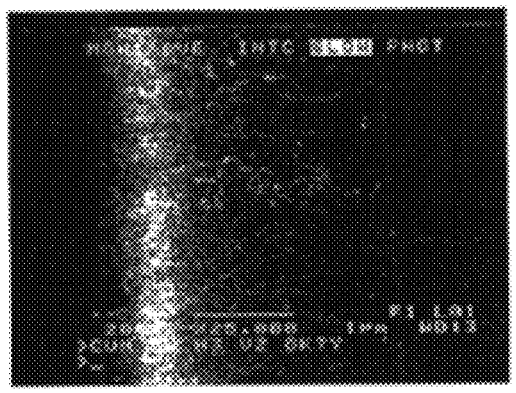
FIG. 6c is an SEM image of an embodiment of nanotubes grown at a temperature of 500° C. according to the invention.
Figure 6D:
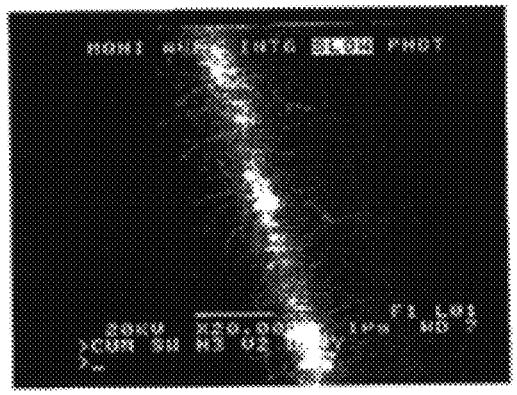
FIG. 6d is an SEM image of an embodiment of nanotubes grown at a temperature of 550° C. according to the invention.

FIG. 5 shows a scanning electron microscope (SEM) image of the results of patterned growth using one preferred low-temperature growth method comprising: annealing the substrate (30 minutes at 653° C.) prior to growth, followed by plasma assisted growth under a gas pressure 5 Torr (90% ethylene, 10% hydrogen) with a dc bias of about 100V. In the example shown in FIG. 5, an Fe catalyst was utilized. The catalyst was sputtered on the silicon substrate at a thickness of between about 0.3 to 1.0 nm. Using a similar such technique a series of high resolution tunneling electron microscope (HRTEM) images of nanotubes grown at temperatures from as low as 411 to 550° C. using a NiTi catalyst are shown in FIGS. 6a to 6b.

While the self-assembled bimorphs contemplated in the embodiments discussed so far have been constructed of carbon nanotube bimorphs made from pyrolizing an ethylene feedstock over a substrate having an ordered array of nucleation points, the bimorphs can be of any shape and made by any process and from any material suitable for making self-assembled nanobimorphs, such as, for example, spheres or pyramids made of other atomic materials or even biomolecules, such as, for example, proteins. In another embodiment, the bimorphs are further functionalized for a variety of applications, such as, for example, being made hydrophilic or hydrophobic, being charged either negatively or positively, or being derivatized with specific chemical groups, etc. In addition, although only an untreated carbon nanotube nanomechanical device have been shown thus far, in situ sidewall treatments could further increase the tube-to-tube contact resistance, to increase the charge differential induced by a given applied voltage.

In addition, although in the embodiments shown thus far the nanomechanical device 10 according to the present invention comprises a pair of vertically aligned nanotubes 20 and 22 grown on e-beam written catalyst dots 24 with integrated electrodes 14 and 16, as shown in FIG. 1. Any spacing or pattern of catalyst dots 24 and electrodes 20 and 22 may be utilized such that the van der Waals attraction between adjacent tubes is sufficient to ensure that the tubes become attached along their sidewalls at their distal ends, as shown in FIG. 1. In addition, while the embodiments shown thus far described a pair of nanotubes (one on each electrode), the present invention could also function as an effective actuator or oscillator using multiple tubes grown on each electrode, and could provide greater actuation forces, for example in that configuration. Alternatively, actuators and force sensors with more than two electrodes are also possible and would enable motion and detection in more than a single plane of operation.

Although as discussed above, an oscillator geometry comprising a nanobimorph with electrical contacts to both nanotubes is preferred, any suspended nanobimorph structures with a bias source capable of controllably applying a bias between the nanotubes or alternatively for measuring the bias across the nanotubes in a detector mode may be utilized. For example, systematic variations of critical geometric factors may include the nanotube lengths and electrode attachment. As another example, it is also possible to produce a nanobimorph in the plane of the substrate, suspended over a trench.

Finally, although the above discussion has focussed on the construction and structure of the nanobimorphs, it should be understood that a nanomechanical device according to the invention may also include a body, a self-contained power supply, and any additional machinery or circuitry necessary for the device's operation. For example, the body of the nanomechanical device itself can be made of any material suitable for micromachining utilizing standard lithographic or MEMS techniques to enclose the bimorph, such as, for example, aluminum oxide or silicon. In a preferred embodiment, the body further comprises a cap layer which can be of any design such that the cap layer protects the bimorph from unwanted contact with the external environment. Such a cap layer could be made of any suitable material, such as, for example, aluminum oxide or silicon. Such a cap layer could be formed by any conventional MEMS process, such as growth or deposition over a sacrificial layer (not shown) deposited to encapsulate the self-assembled nanobimorph wherein the sacrificial layer can subsequently be removed to expose the self-assembled nanobimorph itself. Alternatively, these support structures could be formed in a single deposition step with the self-assembled nanobimorph. In a more preferred embodiment, one of the substrate, the cap layer, or walls of the nanomechanical device is transparent such that an optical source can be used to interrogate or activate the nanobimorph.

In another alternative embodiment the nanomechanical device comprises an array of multiple nanobimorphs aligned on a single substrate such that multiple or parallel processing can be carried out at one time. In this embodiment, the bimorphs can be integrated into a single circuit or detector. It should be understood that while arrays of bimorphs are discussed above, any suitable alternative geometry of bimorphs may be utilized. Such an embodiment could be used to develop a mobile bimorph detector device on a chip for mobile detection and analysis of samples. In such an embodiment a portable power source (not shown) would also be integrated into the device.

Although specific embodiments are disclosed herein, it is expected that persons skilled in the art can and will design alternative nanomechanical devices and methods to produce the nanomechanical devices that are within the scope of the following claims either literally or under the Doctrine of Equivalents.

What is claimed is:

1. A nanomechanical device comprising:
   a power device comprising at least one of a power emitter and a power detector;
   a substrate;
   and at least one self-assembled nanobimorph in signal communication with the power device wherein each nanobimorph comprises at least two adjacent nanofeatures having proximal and distal ends, wherein the proximal ends of the nanofeatures are spaced apart and fixedly attached to the substrate and wherein the distal ends of the nanofeatures are attractively coupled such that a potential applied to the nanobimorph by the power device induces lateral motion in the nanobimorph and such that motion of the nanobimorph induces a voltage or current measurable by the power device.

2. The nanomechanical device according to claim 1 wherein the substrate is made of a material selected from the group consisting of silicon, alumina, glass or plastic.

3. The nanomechanical device according to claim 2 wherein the substrate further comprises a plurality of electrodes sufficient such that each of the nanofeatures is fixedly attached to the substrate through a separate electrode, wherein the electrodes are in signal communication with the power device and wherein the nanobimorphs are in signal communication with the power device through the electrodes.

4. The nanomechanical device according to claim 3 wherein multiple nanofeatures are attached to each electrode.

5. The nanomechanical device according to claim 1 wherein the electrodes are made of a metal selected from the group consisting of gold, platinum and titanium.

6. The nanomechanical device according to claim 1 wherein the substrate further comprises a plurality of catalytic spots deposited thereon wherein each of the nanofeatures is fixedly attached to the substrate through a separate catalytic spot.

7. The nanomechanical device according to claim 6 wherein the catalytic material is selected from the group consisting of Fe, Ti, Ni, Co, Ni/Co alloy, and Ni/Ti alloy.

8. The nanomechanical device according to claim 1 wherein the power device is a power source selected from the group consisting of: a light source, a voltage source, a current source, and a magnetomotive source.

9. The nanomechanical device according to claim 1 wherein the power device is a voltage detector.

10. The nanomechanical device according to claim 1 wherein the nanofeatures have a cross-sectional dimension of about 1 to 100 nm.

11. The nanomechanical device according to claim 1 wherein the space between the nanofeatures of a single bimorph has dimensions of about 10 to 200 nm.

12. The nanomechanical device according to claim 1 wherein the device operates as one of an actuator, an oscillator and a sensor.

13. The nanomechanical device according to claim 1 wherein the device is an actuator selected from the group consisting of: a probe, a nanotweezer, a molecular assembly device, a switch, and a mechanical transistor.

14. The nanomechanical device according to claim 1 wherein the device is an oscillator selected from the group consisting of: a filter, a signal processor, and a microgyroscope.

15. The nanomechanical device according to claim 1 wherein the device is a force-based sensor.

16. The nanomechanical device according to claim 1 wherein the comprises a plurality of nanobimorphs arranged on the substrate in a uniform periodic array having a uniform lattice spacing between nanobimorphs.

17. The nanomechanical device according to claim 1 wherein the nanofeatures are made of carbon.

18. The nanomechanical device according to claim 1 wherein the nanofeatures are grown by self-assembly on the substrate.

19. The nanomechanical device according to claim 1 wherein the nanofeatures are one of either nanotubes or nanorods.

20. The nanomechanical device according to claim 1 wherein the nanofeatures are chemically or biologically functionalized.

21. The nanomechanical device according to claim 1 wherein the outer surface of the nanofeatures are treated to increase the resistance of the nanofeatures.

22. The nanomechanical device according to claim 1, further comprising a device body defining an internal volume wherein the nanobimorph is confined within the internal volume.

23. The nanomechanical device according to claim 22, wherein one of the substrate or device body is transparent.

24. The nanomechanical device according to claim 22 wherein the device body is made of a material selected from the group consisting of silicon, alumina, glass and plastic.

25. The nanomechanical device according to claim 1 wherein the potential induced motion of the nanobimorph is proportional to the potential applied to the nanobimorph.

26. The nanomechanical device according to claim 1 wherein the motion induced potential of the nanobimorph is proportional to the degree of motion of the nanobimorph.

27. The nanomechanical device according to claim 1 wherein the device is disposed in a liquid environment.

28. The nanomechanical device according to claim 1 wherein the device is disposed in a vacuum environment.

29. The nanomechanical device according to claim 1 wherein the device is disposed in a gaseous environment.

30. The nanomechanical device according to claim 1 comprising at least two nanobimorphs wherein at least one of the nanobimorphs is operated as a sensor and at least one of the nanobimorphs is operated as an actuator.

31. The nanomechanical device according to claim 1 comprising at least two nanobimorphs wherein the nanobimorphs are operated as sensors, wherein each sensor is designed to detect a different substance.

32. The nanomechanical device according to claim 1 comprising at least two nanobimorphs wherein the nanobimorphs are operated as sensors, wherein all the sensors are designed to detect a single substance.

33. The nanomechanical device according to claim 1 comprising at least two nanobimorphs wherein the nanobimorphs are operated as actuators to provide motion in multiple dimensions.

34. The nanomechanical device according to claim 1 wherein the substrate further comprises a depressed portion and where the nanobimorph is formed over the depressed portion in the plane defined by the substrate.

35. The nanomechanical device according to claim 1 wherein the substrate has an area of about 1 $mm^2$ to 1 $cm^2$.

36. A nanomechanical device comprising:

a power detector;

a substrate;

and at least one self-assembled nanobimorph in signal communication with the power detector wherein each nanobimorph comprises at least two adjacent nanofeatures having proximal and distal ends, wherein the proximal ends of the nanofeatures are spaced apart and fixedly attached to the substrate and wherein the distal ends of the nanofeatures are attractively coupled such that motion of the nanobimorph induces a voltage or current measurable by the power detector.

37. A method of detecting a molecule in a sample comprising the steps of:

providing a nanomechanical device comprising a power detector, a substrate, and at least one self-assembled nanobimorph in signal communication with the power detector wherein each nanobimorph comprises two adjacent nanofeatures having proximal and distal ends, wherein the proximal ends of the nanofeatures are spaced apart and fixedly attached to the substrate and wherein the distal ends of the nanofeatures are attractively coupled such that motion of the nanobimorph induces a potential measurable by the power detector;

introducing the sample into proximity of the nanomechanical device;

measuring the potential on the bimorph and communicating the potential to a user.

38. The method according to claim 37 wherein the potential is proportional to the motion of the nanobimorph.

39. The method according to claim 37 wherein the nanofeatures are nanotubes.

* * * * *

UNITED STATES PATENT AND TRADEMARK OFFICE
CERTIFICATE OF CORRECTION

PATENT NO. : 6,756,795 B2
DATED : June 29, 2004
INVENTOR(S) : Hunt et al.

It is certified that error appears in the above-identified patent and that said Letters Patent is hereby corrected as shown below:

Title page,
Item [75], Inventors, "Brian D. Hunt" delete "La Cresenta", insert -- La Crescenta --.
Item [56], References Cited, OTHER PUBLICATIONS, "Liu, Q. et al.; Detection of Virtually..." reference, delete "Sensitity", insert -- Sensitivity --; "Murakami, Hirohiko et al.; Field emission..." reference, delete "pattterned", insert -- patterned --; "Poncharal, Philippe et al.; Electrostatic Deflections..." reference, delete "Resonance", insert -- Resonances --.

Column 12,
Line 46, after "wherein the", insert -- device --.

Column 14,
Line 26, after "mechanical device;", insert -- and --.

Signed and Sealed this

Fourth Day of October, 2005

JON W. DUDAS
*Director of the United States Patent and Trademark Office*